US012406357B2

(12) United States Patent
Matarazzo et al.

(10) Patent No.: US 12,406,357 B2
(45) Date of Patent: Sep. 2, 2025

(54) CROP SCOUTING INFORMATION SYSTEMS AND RESOURCE MANAGEMENT

(71) Applicant: ADAVIV, Somerville, MA (US)

(72) Inventors: Thomas James Matarazzo, Astoria, NY (US); Mohammad Mahmoudzadehvazifeh, Medford, MA (US); Ian Shaun Seiferling, Somerville, MA (US)

(73) Assignee: AdaViv, Somerville, MA (US)

( * ) Notice: Subject to any disclaimer, the term of this patent is extended or adjusted under 35 U.S.C. 154(b) by 454 days.

(21) Appl. No.: 17/758,413

(22) PCT Filed: Jan. 5, 2021

(86) PCT No.: PCT/US2021/012184
§ 371 (c)(1),
(2) Date: Jul. 6, 2022

(87) PCT Pub. No.: WO2021/141897
PCT Pub. Date: Jul. 15, 2021

(65) Prior Publication Data
US 2023/0049158 A1 Feb. 16, 2023

Related U.S. Application Data

(60) Provisional application No. 62/957,640, filed on Jan. 6, 2020, provisional application No. 62/957,644, filed
(Continued)

(51) Int. Cl.
*G06K 9/00* (2022.01)
*A01B 69/04* (2006.01)
(Continued)

(52) U.S. Cl.
CPC .......... *G06T 7/0012* (2013.01); *A01B 69/008* (2013.01); *A01M 7/0089* (2013.01);
(Continued)

(58) Field of Classification Search
CPC ............ G06T 7/00; G06K 9/00; H04N 7/188
(Continued)

(56) References Cited

U.S. PATENT DOCUMENTS

2014/0035752 A1  2/2014  Johnson
2017/0030877 A1  2/2017  Miresmailli et al.
(Continued)

FOREIGN PATENT DOCUMENTS

KR    10-1811640 B1    12/2017

OTHER PUBLICATIONS

Low cost colour sensors for monitoring plant growth in a laboratory; Mark Seelye et al.2011 IEEE (Year: 2011).*
(Continued)

*Primary Examiner* — Seyed H Azarian
(74) *Attorney, Agent, or Firm* — Womble Bond Dickinson (US) LLP; John V. Forcier

(57) ABSTRACT

Described herein are techniques for generating contextually rich plant images. A number of data captures of raw plant data are generated via a sensing unit configured to navigate a growing facility. Metadata is generated and assigned to the raw plant data including at least one of: plant location, timestamp, plant identification, plant strain, facility identification, facility location, facility type, health risk factors, plant conditions, and human observations. Images generated by the sensing unit are analyzed and pixel annotations are generated in the images based on their relation to one or more plant well-being features. Data tags are generated and assigned the data captures based on an analysis of the data captures. The data tags are text phrases linking a particular data capture to a specific threat to plant well-being.

12 Claims, 9 Drawing Sheets

Related U.S. Application Data on Jan. 6, 2020, provisional application No. 62/967,227, filed on Jan. 29, 2020.

(51) Int. Cl.

| | |
|---|---|
| *A01M 7/00* | (2006.01) |
| *A61K 35/12* | (2015.01) |
| *B64C 39/02* | (2023.01) |
| *G01N 33/00* | (2006.01) |
| *G05D 1/00* | (2006.01) |
| *G06F 3/04847* | (2022.01) |
| *G06T 7/00* | (2017.01) |
| *G06V 10/70* | (2022.01) |
| *G06V 10/77* | (2022.01) |
| *G06V 10/774* | (2022.01) |
| *G06V 20/10* | (2022.01) |
| *B64U 101/00* | (2023.01) |
| *G06V 10/82* | (2022.01) |

(52) U.S. Cl.
CPC ....... *B64C 39/024* (2013.01); *G01N 33/0098* (2013.01); *G05D 1/0219* (2013.01); *G06F 3/04847* (2013.01); *G06V 10/768* (2022.01); *G06V 10/7715* (2022.01); *G06V 10/774* (2022.01); *G06V 20/188* (2022.01); *B64U 2101/00* (2023.01); *G06T 2207/30004* (2013.01); *G06T 2207/30188* (2013.01); *G06V 10/82* (2022.01); *G06V 2201/06* (2022.01)

(58) Field of Classification Search
USPC ....... 382/100, 103, 106, 110, 153, 155, 162, 382/168, 173, 181, 199, 209, 2, 24, 254, 382/276, 285–289, 305, 317; 700/90, 91
See application file for complete search history.

(56) References Cited

U.S. PATENT DOCUMENTS

| | | |
|---|---|---|
| 2017/0032509 A1 | 2/2017 | Mannar et al. |
| 2018/0039389 A1 | 2/2018 | Martyn |
| 2019/0150357 A1* | 5/2019 | Wu .......................... H04N 7/188 |
| 2019/0259108 A1* | 8/2019 | Bongartz ............... A01G 31/02 |
| 2021/0398281 A1* | 12/2021 | Lys .......................... H04N 23/80 |
| 2022/0272907 A1* | 9/2022 | Geltner ................. A01B 79/005 |
| 2022/0319165 A1* | 10/2022 | Tran ...................... A01G 25/165 |
| 2023/0228725 A1* | 7/2023 | Miresmailli ........ A01M 21/043 |
| | | 700/90 |

OTHER PUBLICATIONS

David Story et al., Lettuce calcium deficiency detection with machine vision computed plant features in controlled environments. Computers and Electronics in Agriculture, vol. 74, issue 2, Nov. 2010.

Massimo Minervini et al., Finely-grained annotated datasets for image-based plant phenotyping. Article in Pattern Recognition Letters, DOI:10.1016/j.patrec.2015.10.013, Nov. 2015.

Marko Arsenovic et al., Solving Current Limitations of Deep Learning Based Approaches for Plant Disease Detection, Symmetry 2019, vol. 11, issue 939, DOI: 10.3390/syml1070939, Jul. 19, 2019.

World Intellectual Property Office, International Preliminary Report on Patentability for PCT/US2021/012183, Jul. 12, 2022, pp. 1-8.

World Intellectual Property Office, International Preliminary Report on Patentability for PCT/US2021/012184, Jul. 12, 2022, pp. 1-6.

* cited by examiner

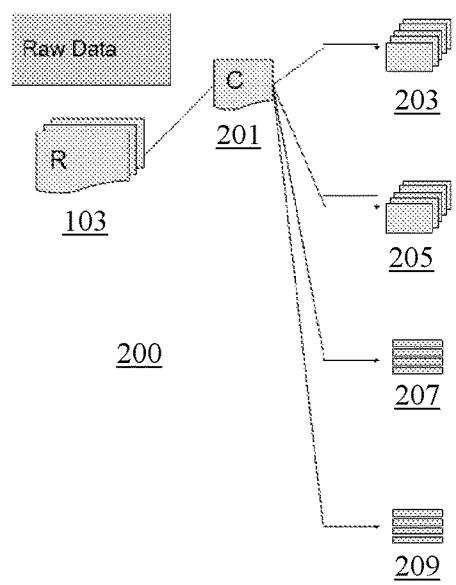
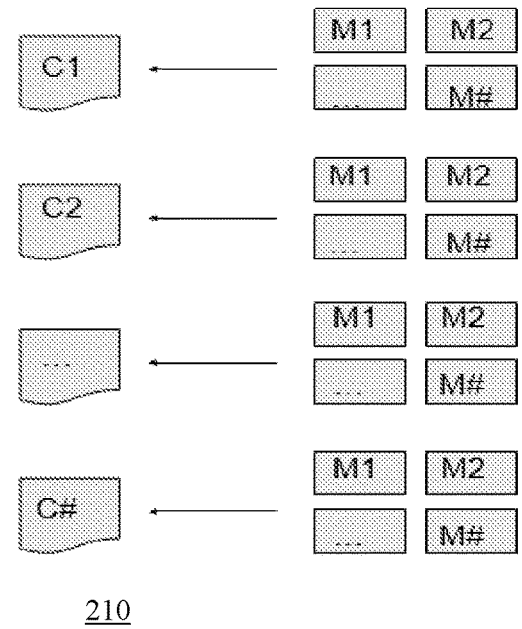
FIG. 2A
FIG. 2B
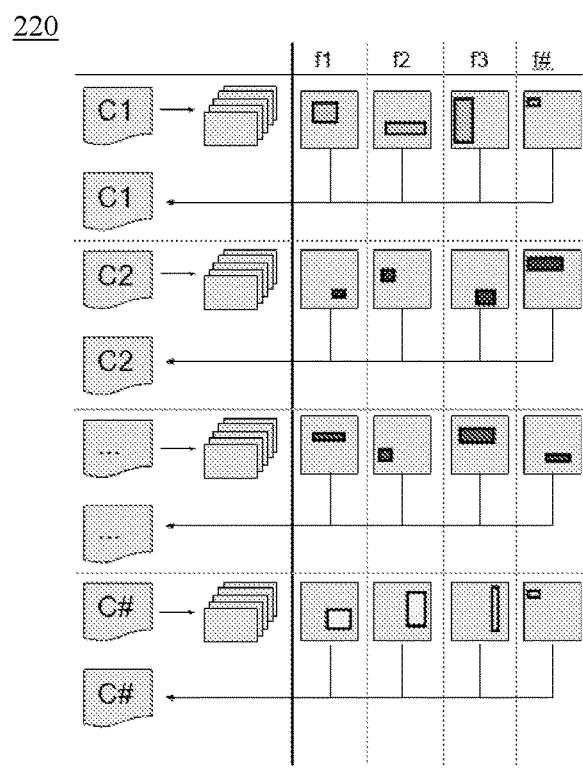
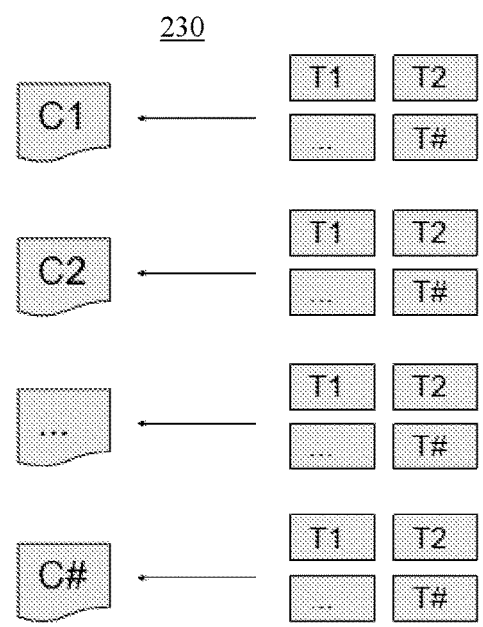
FIG. 2C
FIG. 2D

CROP SCOUTING INFORMATION SYSTEMS AND RESOURCE MANAGEMENT

CROSS-REFERENCE TO RELATED APPLICATIONS

This application is a national stage filing under 35 U.S.C. 371 of PCT/US2021/012184 filed Jan. 5, 2021, and claims priority to and the benefit of U.S. Provisional Application Nos. 62/957,640, filed Jan. 6, 2020, 62/957,644, filed Jan. 6, 2020, and 62/967,227, filed Jan. 29, 2020, the entire disclosures of which are hereby incorporated by reference herein in their entireties.

FIELD OF INVENTION

This disclosure relates to systems and methods for capturing, analyzing, processing, and evaluating data related to growing facilities.

BACKGROUND

Agriculture is the science and art of cultivating plants and livestock. With respect to the production of fruits, vegetables, and other crops, intensive manual labor is required to perform the tedious and often costly processes of farming. In addition, successful farming also relies on the experience and manual observation of experienced growers to identify and improve the quantity and quality of crops produced by, for example, managing growth cycles, environmental impacts, planting and harvesting timelines, disease prevention, etc. All of which, are time-consuming and prone to human error.

Accordingly, it would be advantageous to incorporate automated systems and processes, along with machine learning, to cultivate crops by, for example, monitoring, treating, and harvesting the crops, along with communicating with growers regarding the same.

SUMMARY

Disclosed herein are computer devices and related methods for collecting user inputs, generating information relating to the plants and/or growing environment based on the raw data and user inputs, and displaying same. The systems and methods described herein are configured to provide insights to a grower (or other user), such as, for example, environmental and plant conditions relating to at least one of temperature, plant health status, plant stress status, disease, pests, plant performance, growth status and plant structure, yield predictions, facility mapping, cultivation task records and procedures, diagnostic information related to the mobile sensing unit, the facility, and/or the plants (e.g., a proposed course of action relative a plant, such as more water, apply pesticide, etc.), and temporal and historical data related to all of the foregoing.

In one aspect, the invention relates to a method of generating contextually rich plant images. The method includes generating a number of data captures of raw plant data via a sensing unit configured to navigate rows of benches housing plants within a growing facility; generating and assigning metadata to the raw plant data including at least one of: plant location, timestamp, plant identification, plant strain, facility identification, facility location, facility type, health risk factors, plant conditions, and human observations. The method also includes analyzing images generated by the sensing unit and generating pixel annotations in the images based on their relation to one or more plant well-being features. The method also includes assigning data tags to one or more of the data captures based on an analysis of the data captures, wherein the data tags are text phrases linking a particular data capture to a specific threat to plant well-being.

In various embodiments, the data captures include a collection of images across visible and non-visible light spectra. In some embodiments, the data captures include a collection of thermal images. The data captures can also include a collection of environmental readings including at least one of: temperature, humidity, luminosity, radiation, magnetic field, particulate matter, and chemical compounds. In some embodiments, the data captures include a collection of contextual readings comprising at least one of: acceleration, gyroscope position, orientation, previous system state, next planned system state, power level, CPU usage, CPU memory, and communication signal. The method can also include performing image processing on the images generated by the sensing unit. The image processing can include transforming an image by cropping the image into a smaller image, reducing noise, modifying sharpness or brightness, or performing color balancing; stitching two or more images together to generate a panorama image to minimize double counting plant regions; overlaying different images of a single scene collected with different cameras; or cropping a panorama image to fit a particular aspect ratio. In some embodiments, the method also includes generating a database containing: the raw plant data from the data captures; the metadata assigned to the raw plant data; the pixel annotations in the images; and the data tags assigned to one or more of the data captures. In some embodiments, the method also includes generating a database query based on user input received from a user interface; comparing user input received from the user interface against the data tags assigned to one or more of the data captures; and generating a curated data set including a subset of the data captures corresponding to a combination of the tags, based on the comparison with the user input. In some embodiments, the method also includes generating a plant profile for one or more plants within the growing facility. Each plant profile includes: a plant identifier identifying a particular plant; sensor information generated by the sensing unit related to the particular plant; metadata related to raw plant data of the particular plant; and data tags related to raw plant data of the particular plant.

In another aspect, the present disclosure relates to a method of generating composite plant images. The method includes generating a number of images of the same plant, wherein each of the images differs in focus, resolution, brightness, lighting conditions, or sensor type. The method also includes analyzing the images to determine a common alignment between the images; and superimposing at least two of the images of the same plant to generate a composite plant image.

In another aspect, the present disclosure relates to a method of training a machine learning model. The method includes querying a database containing raw plant data from a number of data captures, metadata assigned to the raw plant data, pixel annotations in images analyzed from the data captures, and data tags assigned to one or more of the data captures wherein the data tags are text phrases linking a particular data capture to a specific threat to plant well-being, and wherein the database query includes at least one tag or data parameter. The method also includes generating a curated training data set including a subset of the data captures corresponding to the at least one tag or data parameter; selecting one or more features from the pixel annotations in images analyzed from the data captures; and building a trained machine learning model based on an analysis of the curated training data set and the one or more features. The trained machine learning model is configured to: receive raw plant data from the data captures; associate a subset of the raw plant data with the one or more features; and identify an existence of one or more plant abnormalities within the subset of the raw plant data based on the association of the subset with the one or more features.

In some embodiments, the tag or data parameter includes a text phrase related to a specific threat to plant well-being such as disease, insects, pest activity, dehydration, nutrient deficiencies, future diseases, harvest yield, or harvest time. When the trained machine learning model identifies the existence of one or more plant abnormalities within a particular plant, the method can also include analyzing raw plant data from previous data captures associated with the particular plant to associate earlier data features with the one or more plant abnormalities. In some embodiments, analyzing raw plant data from previous data captures includes overlaying images of the particular plant from different time intervals to detect a pattern in raw plant data prior to detecting a visible plant abnormality. In some embodiments, the images analyzed from the plurality of data captures include thermal images depicting temperature variations within one or more plants, and the trained machine learning model is configured to identify the existence of one or more plant abnormalities within the subset of the raw plant data based on the temperature variations. In some embodiments, the trained machine learning model is an artificial neural network including a number of input nodes, one or more hidden layers, and a number of output nodes, wherein each input node includes a memory location for storing input values including the raw plant data from the data captures. In some embodiments, the trained machine learning model is also configured to generate a number of risk scores corresponding to the one or more plant abnormalities.

In yet another aspect, the invention relates to a computer-implemented method for processing crop information, the method implementing an application processing system for use in generating and processing information related to environmental and plant conditions within a growing facility and displaying same. In some embodiments, the methods include enhancing the collected or raw data by performing different processes, such as a localization process as described herein. The method includes generating raw data via a mobile sensing unit, where the raw data corresponds to one or more characteristics of one or more plants; receiving user input information in one of multiple available input formats through an input interface; processing the raw data and user input information to create a curated data set that includes processed images representative of the crop information; comparing the curated data set against a pre-existing database of domain data; determining, based at least in part on the comparison of the curated data set, the specific environmental and plant conditions relative to the crop being processed; generating a graphical user interface using a GUI generator; and displaying the information related to the environmental and plant conditions.

In various embodiments of the method, the graphical user interface is interactive and the method further includes manipulating displayed information. In addition, a user will have the capability of "marking events," which can include an analysis of some of all of the raw data through which specific time stamps of interest are deemed to include "significant" or "abnormal" events. Such events can pertain directly to values measured by one or multiple sensors.

In still another aspect, the invention relates to a computer-implemented system for presenting information related to environmental and plant conditions within a growing facility. The system includes a mobile sensing unit including a sensor array and configured to navigate and arrangement of plants within a growing facility and generate raw data corresponding to the plants; an input interface for accepting user input information in one of multiple available input formats; application processing components; and a graphical user interface generator for mediation between the user and application processing components and displaying same. The computer processor components are programmed to perform the steps of collecting the raw data and user input information, validating the data and information, automatically selecting one or more decision engines based on the user input information and a pre-existing database of domain data, selecting a required format corresponding to the selected decision engine from a plurality of available formats stored in a library of decision engine proxies, converting the raw data and user input information into application data according to the corresponding required format, and routing the application data to the one or more selected decision engines to process the application data; generating information related to environmental and plant conditions within the growing facility.

In various embodiments, the computing device includes a display screen, the computing device being configured to display on the screen a menu listing one or more environmental or plant conditions relating to a growing facility, and additionally being configured to display on the screen an application summary that can be reached directly from the menu, wherein the application summary displays a limited list of data related to or derived from the environmental or plant condition information available within the one or more applications, each of the data in the list being selectable to launch the respective application and enable the selected data to be seen within the respective application, and wherein the application summary is displayed while the one or more applications are in an un-launched state.

In yet another aspect, the invention relates to a growth modelling system to track the growth of individual flowers, flower features, fruits, vegetables, or other plant structures (such as stems, branches, nodes, or internodes). The system utilizes at least one of the data collection systems or computer-implemented systems for presenting information related to environmental and plant conditions within a growing facility as described herein, and may be configured to utilize any of the methods described herein. In various embodiments, the individual flower features include at least one of: size, color, surface properties like reflective properties (e.g., shiny or not) or surface covering (e.g., waxy or not), shape and arrangement of flower organelles such as calyces (plural for "calyx"), sex or formation of seeds, leaf-to-bud ratio, color of trichome glands, quality and spatial distribution of trichome glands, and quantity of trichome glands. The invention may also be directing to related methods of modelling plant growth to track the growth of individual flowers, flower features, fruits, vegetables, or other plant structures (such as stems, branches, nodes, or internodes) utilizing any one of the methods described herein. These methods can be used to analyze broader units than a single plant, such a metric for an entire crop or a bench in a crop, or relate to how plants interact with each other (e.g., spacing between plants).

In additional embodiments, the crop monitoring system may include a vision-based system to predict flower or fruit quality (e.g., THC content and Terpene profiles, flavor profiles, ripeness, sugar content, content of other organic compounds) and/or an automated system to harvest and sort plants. The automated harvesting system may utilize the vision-based system (e.g., a scanner) and conveyor system to transport (e.g., via the robotic mechanisms) plants or flowers to different destinations based on plant condition or quality. The crop monitoring systems described herein may include a multi-spectral imaging system to detect unacceptable levels of contaminants in soil, plant, and/or flowers. The systems may rely on a machine learning model configured to identify the unacceptable levels of contaminants (e.g., biological, such as microbial, yeast, virus, or inorganic, such as metals) in soil, plant, and/or flowers based on data from a multi-spectral imaging system and machine learning, which may encompass artificial intelligence and deep learning concepts, such as, for example, the use of classic neural networks.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Accordingly, these and other objects, along with advantages and features of the present invention herein disclosed, will become apparent through reference to the following description and the accompanying drawings. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention and are not intended as a definition of the limits of the invention. For purposes of clarity, not every component may be labeled in every drawing. In the following description, various embodiments of the present invention are described with reference to the following drawings, in which:

FIGS. 2A-2D are schematic representations of exemplary processes of the data enrichment scheme of FIG. 1 in accordance with one or more embodiments of the invention;

DETAILED DESCRIPTION

Figure 1:
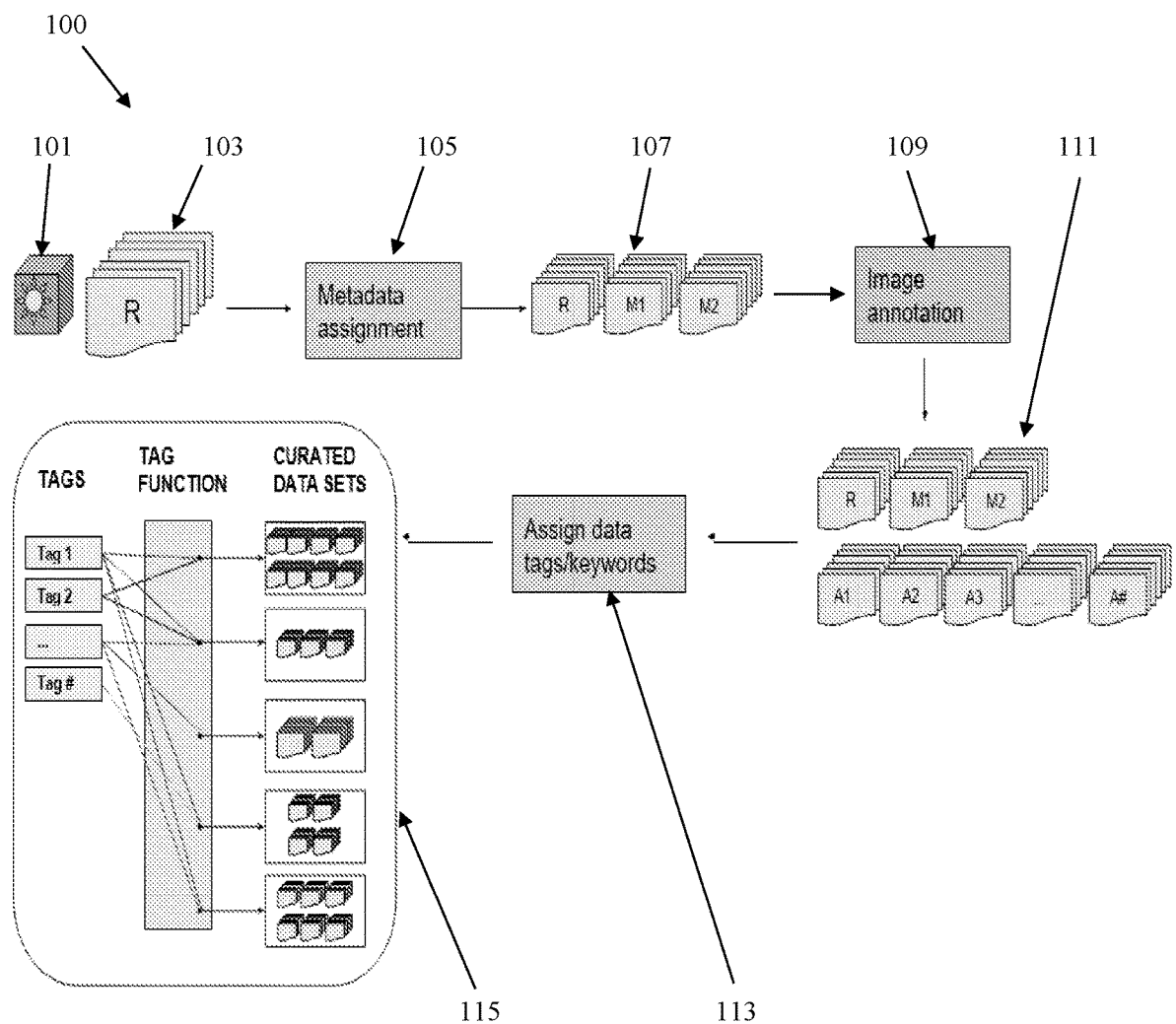
FIG. 1 illustrates a pictorial representation of a data enrichment scheme, in accordance with one or more embodiments of the invention.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

FIG. 1 illustrates a pictorial representation of a data enrichment scheme 100, according to an embodiment of the present disclosure. In this example embodiment, a sensing unit 101, such as a mobile sensing unit, can generate layers of raw data (R) 103. In some embodiments, the mobile sensing unit can be configured to move throughout a facility, either autonomously, via human interaction, or both, collecting data from and interacting with the plants, and in some cases, the benches holding the plants, as well. The mobile sensing unit can include a base that includes a locomotion system, such as a set of wheels or tracks coupled to, for example, a motor. Other means for propulsion, which would be known to a person of ordinary skill in the art, are contemplated and considered within the scope of the invention. The locomotion system can be mechanically or electronically controlled, either by a controller system operated by a human or as controlled by an autonomous navigation algorithm. The locomotion system and propulsion system will be configured to suit a particular application (e.g., size of the growing facility, terrain, environmental conditions, or environmental regulations). The unit also includes a sensing package or array that can include at least one sensing camera, or other data capturing device, and may include depth sensing and other types of optical or environmental sensing devices.

The raw data 103 captured by the sensing unit 101 can be captured continuously or based on a trigger algorithm, or manual trigger via a software or hardware trigger controlled by human or algorithm, according to various embodiments. This raw data 103 can be saved locally and later transferred to another computing unit or be sent to the cloud on the spot, moments after the trigger, later after the room is scanned, or based on a schedule.

In operation 105, primary data and metadata are created and assigned to the raw data 103 based on sensor data fusion and contextual information (e.g., location, timestamp, multiple camera data fused, or overlaid). In some embodiments, the metadata can also include human input, such as human observations of the target plant conditions. The result of operation 105 is the generation of a first composite dataset 107 including raw data (R) 103 along with metadata (M) attributes produced during operation 105.

In operation 109, the images in the data set are analyzed by a computer or a human inspector, or both, and annotated based on their relation to various features. In some embodiments, the annotations include words or text assigned to the images, or a particular subset of pixels of an image. For example, an inspector can review the images, or raw data 103 generated by the sensing unit 101, and could annotate images by including notes regarding the identification of a particular plant or group of plants, notes about the temperature or growing environment at a certain time, notes about the color of the leaves or moisture of the soil, or any other notes that could be of interest for crop monitoring. In some embodiments, these annotations can be generated and assigned to images by a computer algorithm, rather than a human inspector. The results of operation 109 is a second composite data set 111 that includes the raw data (R) 103, the metadata (M) assigned to the raw data in operation 105, and the annotations (A) assigned to the images in operation 109. In some embodiments, the images (e.g. a capture 203 discussed below in reference to FIG. 2) are contained within the raw data 103, and the annotations are assigned to the images in the raw data.

In operation 113, the second composite data set 111 (i.e., the data including the raw data, metadata, and annotations) is analyzed by a human inspector, a computer, or both. A set of keywords, or "tags" are added to each data capture. These tags are the key to linking data captures to threats to plant well-being, e.g., diseases, insects, pest activities, deficiencies, future diseases, harvest yield, harvest time, etc. The results of operation 113 are a database containing annotated plant data with rich contextual information, including metadata and keywords or tags. This enriched database enables plant data to be queried in new and useful ways, as shown in operation 115. For example, a user can query the database using gestured, written, typed, or spoken user input, and the database can operate as follows: (i) query description is entered in plain English; (ii) the description is broken down into a set of individual tags; (iii) the tags enter a tag function, which analyzes all combinations of the tags and compares them with the tag sets in the database; and (iv) a set of curated data sets is returned, each corresponding to a specific combination of tags.

In one embodiment, a plant database system is queried using a set of tags or keywords, which can include text labels or numbers, or characters associated with a specific condition assigned to the captured data at some point during the data-capture, or during the pre-processing and/or data enrichment. The plant database can also be queried based on one or more scoring criteria, which can be generated during data processing. Scoring criteria can include, for example, a sharpness score, a brightness score, an anomaly score generated using an anomaly detection algorithm, etc. When provided a list of tags and/or scoring criteria, the database system can produce output in the form of the curated data sets discussed above, with one data set for each tag and criteria combination, or a combination of tags and criteria. For example, a user can input a query with a set of six tags presented below in Table 1:

TABLE 1

| Tag 1 | Flowering (crop stage) |
| Tag 2 | OG (cultivar/strain) |
| Tag 3 | F8 (room number) |
| Tag 4 | R1 (row number) |

TABLE 1-continued

| Tag 5 | PM (presence of pathogen) |
| Criteria 1 | sharpness_score > 0.8 AND anomaly_score_model_1 > 0.1 |

With the six tags identified in the query, the system can produce a curated data set that corresponds to each individual tag and their combinations, as illustrated in Table 2:

TABLE 2

| Set 1 | Flowering + OG |
| Set 2 | OG + F8 |
| Set 3 | Flowering + OG + PM |
| Set 4 | Flowering only |
| ... | ... |

One skilled in the art will appreciate that Table 2 is illustrative only, and the curated data set could include a larger number of data sets than those shown, because there are many more ways to combine the tags and criteria entered in Table 1.

In some embodiments, the input and output arrangements of the database queries can be modified. For example, when provided a set of images (with annotations and tags) belonging to one plant or a set of plants (each with specified plant IDs), the database system can perform a query based on the images, rather than the tags, and produce output in the form of plant ID #s (or corresponding datasets for these plants) based on certain matching conditions. Matching conditions can either be specified by the user or determined automatically by a computer. This is analogous to when online audio or video streaming services make music or video recommendations based on a user's past activity; in this case, the system is recommending a user consider data on the performance of certain plants that were seen previously in order to better understand the one under consideration. This information would serve useful when it comes to making predictions on important plant features, such as, for example, yield, and content and profiles of organic compounds such as THC, terpenes, flavonoids, phenolic acids, and carotenoids etc. or to predict the outcome(s) of proposed actions or decisions. The data filtering or querying process can also be used to select data for annotation (e.g., for the machine learning process of active learning or in more general for creating a curated dataset for annotators to highlight image regions or enrich images with some user-input based on the annotation guidelines).

In one example embodiment, the database system is queried with a set of 100 images from plant #599, and the system can analyze those images of that particular plant and produce lists and suggestions similar to those presented below in Table 3:

TABLE 3

| Most similar bud development | Plant #100 |
| Most similar size | Plant #226 |
| Most similar growing environment | Plant #788 |

In another example embodiment, the database system can generate a plant profile for each or a subset of the plants within the growing facility. Each plant profile can include, for example, a plant ID, as well as any other data collected or generated about that particular plant. The data can include sensor information, metadata, tags, or any other data particular to each plant. In this way, each plant can have a "digital fingerprint" and a unique ID, and an inventory of each plant can be built. With each plant having a unique plant profile, additional data can be collected and added to that profile throughout a crop cycle. The identity of the plant can be determined, for example, by scanning an RFID-like tag on or near the plant, a handwritten tag, using visual cues, based on predetermined reference points, sensor data, routing information from the mobile sensors, etc. This type of precise tracking information can be utilized for various purposes, e.g., compliance, inventory, supply chain management, genuine "seed-to-sale" systems, etc.

As used herein, the term "tags" describes text words or phrases or numbers that can be manually or automatically added to an individual data capture, e.g., an entire image. Tags can include, for example, facility ID, facility location, plant type, plant strain, geometry information, time of year, known disease conditions, etc.

As used herein, the term "scoring criteria" describes a score or value generated and assigned to a data capture. Scoring criteria can include, for example, a sharpness score, a brightness score, an anomaly score generated using an anomaly detection algorithm, etc.

As used herein, the term "features" describes numerical or identifiable patterns that can be determined based on analyzing some annotated imagery data. Features can correspond to physical objects, physical phenomena, other shapes, etc. occurring within a portion of an image. Examples of features include: flower bud, mildew spot, leaf, etc.

The term "image data" may refer to a combination of multiple images from various wavelengths, and may be different from what a human can see in person. This means that certain features may not be strictly "visible patterns," but instead can be patterns or trends found in numbers (aka "numerical patterns") that have been determined by an AI algorithm (Note: a computer can convert "image data" to "numerical data" during processing).

FIG. 2A illustrates a pictorial representation of an example data capture process 200, according to an embodiment of the present disclosure. As discussed above in reference to FIG. 1, a sensing unit can generate a set of raw data (R) 103. This raw data 103 can include individual captures (C) 201, which can each include a collection of raw data collected by a variety of sensors within a sensing array that share a timestamp. For example, a first capture 203 can include a collection of images across a light spectrum. A second capture 205 can include, for example, a collection of thermal images. A third capture 207 can include, for example, a collection of environmental readings including temperature, humidity, luminosity, radiation, magnetic field, particulate matter, and chemical compounds. A fourth capture 209 can include, for example, a collection of contextual readings related to the sensing device including acceleration, gyroscope, position, orientation, previous system state, next planned system state, power level, CPU usage, CPU memory, and communication signal.

FIG. 2B illustrates a diagram of an example process 210 for assigning metadata to data captures, according to an embodiment of the present disclosure. Each capture (C1, C2 . . . C#) can be assigned one or more metadata components based on an analysis of some or all of the raw data and/or a previous data analysis. Metadata may also be developed based on contextual sensing information, site specific information, or other qualitative variables. Metadata can include, for example, timestamps, plant ID, plant strain, precise plant location, facility ID, facility type, facility location, or pre-exposed health risk factors. In some example embodiments, a first set of metadata (M1, M2 . . . M#) is created and assigned to the first capture, C1, in the raw data. A second set of metadata can be created and assigned to the second capture C2, in the raw data. This second set of metadata may or may not be the same as the first set of metadata, and the metadata generation and assignment process can be repeated for all captures in the raw data.

FIG. 2C illustrates a diagram of an example image annotation process 220, according to an embodiment of the present disclosure. As discussed above in FIG. 1, and with specific reference to operation 109, the images and thermal images can be annotated by a computer or a human operator. In one embodiment, the images (203) and thermal images (205) can be collected from each capture, e.g., C1. These images can be divided into sessions, which are sets of images that are shown to annotators (people who are trained to highlight conditions of interest in the images shown to them), or shown to a machine learning algorithm trained to identify and high-light conditions of interest in the images. In some embodiments, the images might already be pre-initiated with some computer guesses in a workflow where annotators correct machine-generated predictions or assignments (referred to as Active Learning). In one example embodiment, data annotation includes at least two operations: (i) pixel(s) selection for highlighting a condition/ anomaly; and (ii) whole-image class assignment for a specific condition or a set of conditions. Initially, a set of pixels from an image is selected based on its correspondence to one or more predefined data features, e.g., f1 or f2. Next, the selected pixels can be assigned numeric values based on an image-feature analysis. The process repeats for all features and images. The annotations become embedded into the second composite data set 111. FIG. 2C exemplifies the pixel selection process of all features, e.g., f1, f2, f3, etc., for one image in a data capture. The data annotation task has different embodiments, such as bounding box drawings or paint brush, for different types of image segmentation. The operation of this process results in data comprising raw data, metadata, and image annotations, FIG. 2D illustrates a diagram of an example process 230 for assigning keywords or tags to data captures, according to an embodiment of the present disclosure. In some embodiments, after image annotation is complete, an analysis is conducted on the second composite data set 111 in order to assign a set of words (alphanumeric phrases, tags, or keywords), hereby "tags", to each capture. These tags become embedded into the data set. Tags can include, for example, text phrases that link the data to specific threats to plant well-being, e.g., diseases, insects, pest activities, deficiencies, future diseases, harvest yield, harvest time, etc. In one example embodiment, a first set of tags (T1, T2 . . . T#) is created and assigned to the first capture, C1. A second set of tags can be created and assigned to the second capture, C2. This second set of tags can be the same or different from the first set of tags. The tag generation and assignment process can be repeated for all captures.

Figure 3:
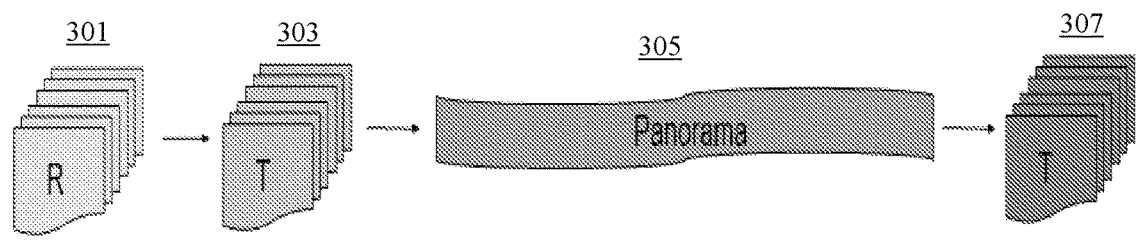
FIG. 3 illustrates a pictorial representation for an example image processing method in accordance with one or more embodiments of the invention.

FIG. 3 is a pictorial representation for an example image processing method, according to an embodiment of the present disclosure. In one example embodiment, the raw data 301 can be processed to generate transformed images 303. The transformed images 303 can include cropped smaller images, augmented images, images with reduced noise, or modified images with increased or decreased brightness, sharpness, etc. The transformation process can also standardize attributes by performing perspective or color transformation (white/color balancing). These operations can be done, for example, on a computing device that initially records the data or on a separate computing device that receives the images at a later time. The transformation can be done via machine learning algorithms, such as de-noising auto-encoders. The pre-processing or post-processing can be any process that transforms each initial/raw image 301 into another transformed image 303. Each image can be transformed in to potentially multiple images for the purpose of model training or at the time of inference. The transformed images can be saved to be used at a later time, or transformation can be done on demand at the time of learning or inference. In a similar fashion, the data produced during the data enrichment process discussed above in reference to FIG. 1 can be modified or transformed into different forms. The data transformation can happen at different stages of data journey, and based on that it may be called pre or post processing. In some embodiments, each transformation can be rule-based or be based on a machine learning model.

Either raw images 601 or transformed images 603 can be combined or "stitched" together into a panorama 305 representing a bench or row of plants. This can be performed, for example, by a process called image stitching and geometric image processing. Using this process, double counting of overlapping regions, which can exist in images captured consecutively, can be minimized.

The one or more panorama images 305 can be further processed in order to crop them, down-sample or up-sample, or overlay the images. In one example embodiment, after stitching a subset of the images into a panorama image 305, the images can be cropped into smaller chunks 307 to be fed into various machine learning architectures, which expect images of certain sizes (e.g., an image that is 3570×5750 can be divided into overlapping or non-overlapping regions of 128×128 for which we have human input mask images of the same size or image-level tags, where masks are a set of pixels that were highlighted by annotators to belong to a certain condition/segment class). These images can then be used as ground-truth data for model training or validation, or to produce machine predictions at the time of inference. The output of each crop can be post-processed individually or collectively with other crops to represent the final insights.

In some embodiments, images can be down-sampled or up-sampled, which may depend on the model training or inference task at hand. A different transformation may be applied for certain model training and/or inference, in which multiple images of captured data based on a certain scene can be combined to generate a higher resolution image of the same scene. In some embodiments, the down-sampling or up-sampling transformation can be a machine learning model itself or trained based on the ground-truth data collected previously.

In one example embodiment, different images of the same scene, collected with the same or different cameras and triggered simultaneously or at different times, can be transformed to produce an overlaid hyper-image in which each pixel data represents the values collected in different images in a process called pixel-level matching. This may involve image rotation/shift or a more complex transformation to achieve pixel level matching. This process can be rule-based or based on a machine learning model trained based on previously collected ground-truth data.

Figure 4:
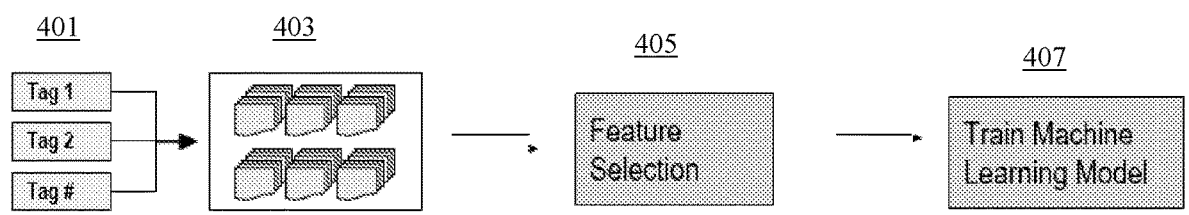
FIG. 4 illustrates a pictorial representation of an example model training process in accordance with one or more embodiments of the invention.

FIG. 4 is a pictorial representation of an example model training process, according to an embodiment of the present disclosure. In operation 401, a set of tags and/or scoring criteria are used to query a database (as described above in reference to operation 115 of FIG. 1), and a curated data set 403 is retrieved. In some embodiments, the curated data set 403 can be generated or retrieved by setting particular data parameters and file parameters. For example, a user may only be interested in a set of data that has a powdery mildew tag, or the data for a specific strain of plants at a certain stage of development and with a certain condition.

In operation 405, the features, e.g., f1, f2, f3, etc. to be considered in the machine learning model or for the purpose of creating a rule-based inference are selected. The features were appended to the data during data annotation (operations 109 and/or 113). These features can be selected manually or by using an AI model using various deep learning architectures in a supervised, unsupervised, or semi-supervised manner. In one embodiment, features can be selected using an AI model by directly feeding post-processed or raw images into a model architecture.

In operation 407, a machine learning model is trained based on the curated data set and data features. In another example embodiment, the model can be trained based on raw images, cropped or uncropped images, or transformed or untransformed images.

According to an example supervised training technique, the curated data set 403 and the enriched data associated with that data set, either transformed or raw, can be fed into a particular machine learning model architecture with an optimization algorithm that adjusts or tailors the model parameters with the goal of generating an output that can replace or help humans in the generation of enriched data. In some embodiments, the model output can be a condition class for each image fed into the model, or a mask. The supervised training can include, for example, highlighting a set of pixels on the image associated with a condition or a set of conditions, or highlighting an array representing an inference vector for each pixel in the image (also referred to as a multidimensional array or tensor).

The severity of a condition can be represented as a numerical value or a set of numerical values for each pixel in the image. The training job can be started from scratch by initiating model parameters to random values, or the model parameters can be initiated to values based on a previously trained model trained on a separate dataset. In some embodiments, different models can be trained for highlighting different conditions separately, or a single model architecture capable of generating multiple predictions for different classes can be trained simultaneously. The model output can be transformed into various forms to be shown to end-users at plant-level, bench-level, or even row or room-level. In some embodiments, each bench or plant can be assigned a normality or abnormality score that can be represented to an end user via an interface. For example, a user can be alarmed if a condition is deteriorating over time or when an abnormal or anomalous pattern is detected based on model inference.

According to an unsupervised training model, a machine learning algorithm can be trained to learn usual or normal distributions so that it can detect when an instance of data contains an anomaly. In one embodiment, the model learns to generate the normal version of a given data instance, and by comparing the original data with the produced version it can generate a normality score or normality mask highlighting regions where the produced image and original image differ beyond a certain value. This approach does not require data labels directly, and it only requires training based on a data set that is carefully selected to only contain the "normal" instances during the training.

In some embodiments, generating a whole inference on the raw or post-processed image(s) may require more than a single inference. In some embodiments, the image may be required to be cropped into overlapping or non-overlapping regions, for which inferences are generated. Inferences generated for each crop can then be assembled together or transformed to generate a final insight, which can be represented visually or as a number or a color based on severity of the problem. In some embodiments, inferences can be generated not only for the purpose of insight delivery, but also for the purpose of speeding up the data enrichment process or improving the training of other models. In some embodiments, the system assigns a signature or "fingerprint" to each plant that remains assigned to the plant throughout the various processes and growth structures, such that the system can readily identify and particular plant and/or its location.

According to some embodiments, data augmentation can also be performed. Various rule-based or machine learning techniques can be used to augment new data based on the available data. This may include adding a certain level of noise to data, rotating or shifting images, or changing a color distribution. Data augmentation may also involve using a Generative Adversarial Network to generate new instances of data that do not exist in reality, but to the human eye look very similar to a real image. Such data can then be used as training and or validation data for improving another model's performance.

In some embodiments, in order to speed-up inference or reduce the costs associated with the computation, lighter models can be trained based on the inference of the original models on a set of data. These models may have lighter architectures than the original ones, and as soon as they can produce high enough accuracy results by validating them on a ground-truth data set (which can also be a subset of inferred data) they can replace the original models in producing inferences in production.

In some embodiments, once a model has been trained, the model can receive raw data or a curated data set, associate a subset of the data with one or more features of interest, and identify the existence of a plant condition or a plant abnormality based on the association of the subset of the data with the features of interest.

In some embodiments, a trained model can detect an issue or abnormality within one or more plants before the issue or abnormality is detectable by a human. If a trained model detects an issue or abnormality at a certain stage of development for a plant or set of plants, a user can look into prior data of the same plant in order to associate that condition with a prior data set or feature. In this way, the strength of a model in detecting an issue earlier in time can be improved, even when there is no clear feature visible to a human eye. In some embodiments, image overlaying can be used to best approximate pixel-wise matching between images captured consecutively with a time interval that can range from a few hours to a few days. In the model training process, the earlier images with highlighted regions based on the later images are passed to the model in order to see if the model can learn to detect patterns earlier than initially detected by the original model. The parameters of this new model may be initiated to the parameters of the original model at the start of a training job. The validation can then be done on a subset of ground-truth data not used during the process of training. In some embodiments, earlier detections can trigger certain actions by humans or by machines to minimize the risks of negative impacts on the crop KPIs (e.g., yield).

In additional embodiments, the sensing system is configured to perform various data capture steps that provide for plant-level localization for providing plant-level stress mapping and analytics insights to growers to improve cultivation by loss prevention through optimal and targeted treatments. Performing localization processes may further enhance the data and insights by reducing or eliminating errors (e.g., false positives), improving resolution and focus for providing insights to the grower. As previously described, the sensing system 101 scans rows of plants and automatically or manually through the use of human input via software assigns certain location information. This can be done completely manually to completely automated or using a hybrid approach through a combination of techniques including, but not limited to, QR code detection, wheel and visual odometry. In some cases, this step of segmenting the data and assigning it to room/row or more granular regions levels may not be enough to do a 1:1 mapping between raw or processed collected data to individual plants, in which case, 3D mapping can improve this process. Additionally, during data/image collection and/or data/image processing, the system may assign a signature or "fingerprint" to each plant that remains assigned to the plant throughout the various processes and growth phases, such that the system can readily identify a particular plant and/or its location at essentially anytime.

In some embodiments, creating a 3D map of individual plants or pots of plants allows the system/user to detect them in the 3D space. Generally, the term pot is used to designate distinct containers or other unique structures (e.g., hydroponic pods, grow trays, shelves, troughs, etc.) that can be correlated to a particular plant or set of plants. The map can be created using a 3D mapping sensor such as a stereo camera system, LiDAR, or other technologies capable of generating such maps. The fused cloud point of each region of plants can then be segmented before or after preprocessing to correct visual odometry in order to create a cluster of points referring to each plant or pot corresponding to each plant. Next this data is projected into the point-of-view (PoV) from the inferred position of the camera(s) used during the sensing (e.g., as part of 3D scanning or as separate RGB, spectral, or thermal cameras). The projected clusters can then be used as masks for the 2D images collected during the data collection process to provide a 1:1 relationship between individual plants and a subset of data available for each plant in the 2D world.

Other embodiments may use a combination of pot detection as well as inferred plant height profile to generate a simulated model of the individual plant profile before projecting into the 2D point of view of each camera at the time of capture for each capture point. Plant level inferred height profile can be a useful metric to detect growth related characteristics (such as, for example, size, leaf density, growth rate, other nominal features, and anomalies) by itself and can be provided to system users as a 2D or 3D map to high-light regions of interest for treatment, predict growth, and/or to categorize pace of growth for various type of actuations to improve the cultivation operation.

In some embodiments, plant localization approaches include using an IR camera and an RGB camera to collect 2D Images of the plants. A plant mask is created by extracting the pixels associated with plants by, for example, thresholding the pixel values in the image. Specific types of plants may be found using clustering algorithms, such as Kmeans or Hoperaft-Karp. The same plants may be mapped between images using optical flow methods and graphical methods; however, this method has its limitations. For example, images taken of plant canopies are very difficult to segment, even with the human eye. A major reason behind these issues is that the perspective change between images causes the same region of the image to look completely different, resulting in plant segmentations that are not very accurate, often cutting plants in half.

This process may involve creating and fusing two separate point clouds to create a holistic 3D plant and pot profile for the localization purposes and lab calibration techniques used to optimize the fusion parameters and transformation between various camera frames in the 2D and the 3D worlds. Additionally, the depth information can also be overlaid with the 2D pixel values such as spectral RGB and thermal to create an enriched set of data for plant level analytics beyond what a single or set of 2D individual plant data can offer through machine learning techniques, such as various architectures available for 3D convolutional networks. The process may also use QR/April tags, and through real-time detection of those tags, assign the right meta-data about the location where the images where taken and the plants/regions/benches/trays they correspond to. The tags can be detected in the images to help with localization as well as improving the 3D point cloud fusion and addressing noises and artifacts that may arise due to errors in visual odometry.

The data captured and mapped as disclosed above can be used to provide insights to a grower. An auto-scanner records hundreds of gigabytes of data of the plants, etc.; however, the processing of this data is labor intensive if done by hand. Accordingly, as much as possible, the data processing side of providing the data to insight pipeline should be automated, especially, the mapping of plant data.

In some cases, the auto-scanner records plant data based on a timer and without a rigorous mapping between the data recorded and which plant that data is associated with. This means that the insights that the auto-scanner is able to provide has limited precision, specifically for providing insights on a specific plant. While the auto-scanner is able to tell a worker if the plants have an issue, it is not able to tell them which plant. The objective of the data to insights (D2I) pipeline is to connect the raw data generated by the auto-scanner and process it to make plant level insights more accessible. In order to do this the D2I pipeline must include some sort of plant localization, as discussed herein, where plant locations are extracted from raw data generated by the auto-scanner.

In a particular embodiment, the system extends the data from 2D to 3D by using point cloud data, as disclosed above, which allows the system to take advantage of 3D reconstruction algorithms that give data that is relatively consistent across different fields of view. In some cases, this approach includes collecting images of pots (or other containers, etc.) rather than canopy for localization, which allows the system to better estimate plant locations, because the positions are much clearer. Another added advantage is that the system can concatenate the 3D point clouds into a larger bench wide point cloud, allowing the system to analyze the entire bench in one dataset. To further augment the capabilities, the 3D scanning may be done with two cameras. One camera pointing to the canopy and the second camera pointing to the pots, which also allows the system to get a prediction of plant height and also use the pot locations for plant localization. Generally, the process includes creating 3D point cloud reconstruction, mapping point cloud to a world frame, removing distortions introduced by simultaneous localization and mapping (SLAM), extracting pot positions, combining canopy points clouds, and extending solution to two cameras, as described below. In some embodiments, the system uses a depth camera (e.g., the D435i RGBD camera as available from Intel® in Santa Clara, CA) with an onboard inertial measurement unit (IMU) pointed at the plant pots.

To create the 3D point cloud reconstruction, the SLAM algorithm is used and relies on the IMU and visual odometry from the camera. The SLAM algorithm uses Robotic Operating systems (ROS) rtabmap library and outputs a point cloud data (PCD) file, which saves the data as a colored point cloud. One example of a 3D point cloud for a bench is shown at https://share.getcloudapp.com.

Mapping the Point Cloud to a World Frame is carried out in a plurality of steps as follows (see FIGS. 5A-5C). The PCD file is the read using the open3D Python library. The coordinate system of the point cloud 510 has its origin centered at the camera and the axes oriented along the camera look at vector. To better extract insights, the system projects the points into the world frame 500. The coordinate system has the XY plane 502 lying on the table plane, although other systems are contemplated and considered within the scope of the disclosure. Mapping the XY plane onto the table plane includes rotating the axes, globally aligning the measured parameters, estimating the table plane using the least squares, and the local alignment based on a normal vector of the table plane.

The coordinate axis is rotated so that the X axis 502b points along the bench, the Y axis 502a is the camera view at vector and the Z axis 506 points up relative to the camera. Using the camera angle (Beta) and relative height from the camera to the table, the system rotates and translates the coordinate axis accordingly. Global alignment results in the Y axis 502a pointing towards the plants and as parallel to the table plane as possible, with the Z axis 506 pointing up. The XY plane 502 should be as close to the table plane as possible. The table plane is estimated by filtering the point cloud based on the Z coordinate, and keeping points where the absolute value of Z is within some designated or otherwise relevant threshold. The least squares are then used to fit the points to a plane. FIG. 5A also depicts the estimated mesh plane 504. This is before local alignment; thus the coordinate axis is offset from the table plane. FIG. 5B depicts a different view of a similar picture where only the thresholded points are shown and the table plane mesh appears to fit the flat surface created by the points clouds. Local alignment is carried out by calculating a rotation matrix based on a normal vector of the plant. For example, rotate the table plane mesh and then find the Z offset to get a translation vector. With the rotation matrix and translation vector, the system can fine tune the point cloud positions. See FIG. 5C.

Figure 5A:
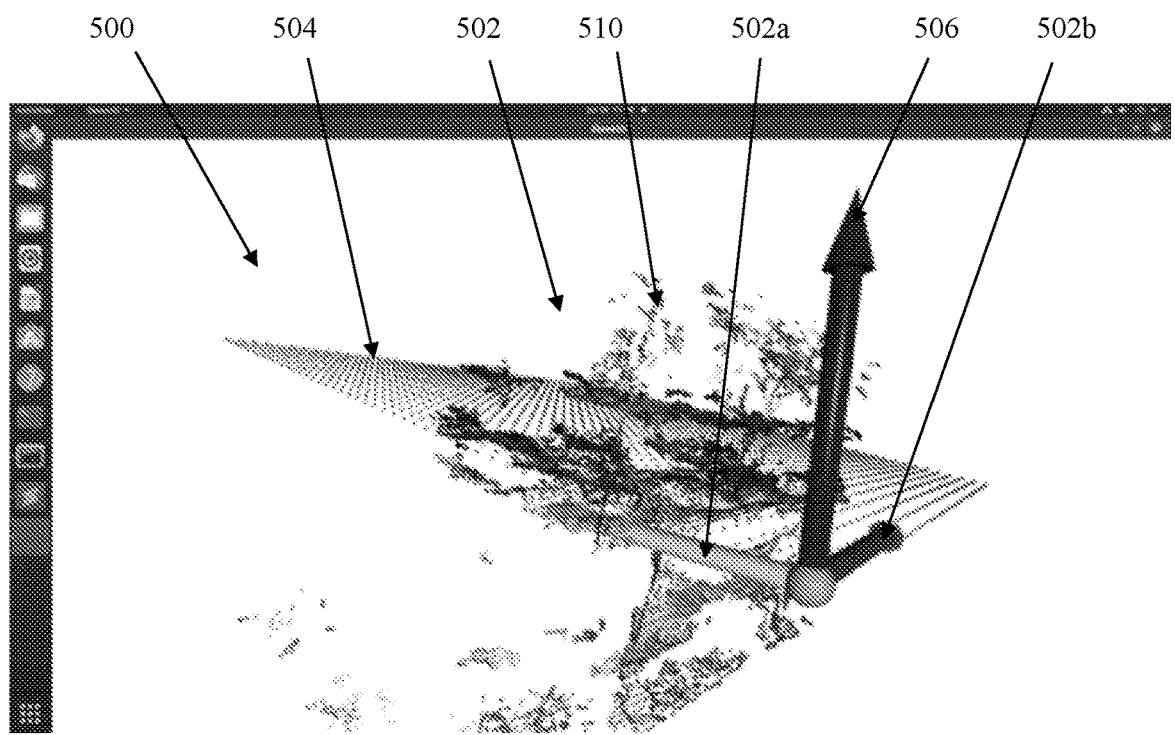
FIGS. 5A-5C are pictorial representations of a process of creating a 3D point cloud reconstruction in accordance with one or more embodiments of the disclosure.
Figure 5B:
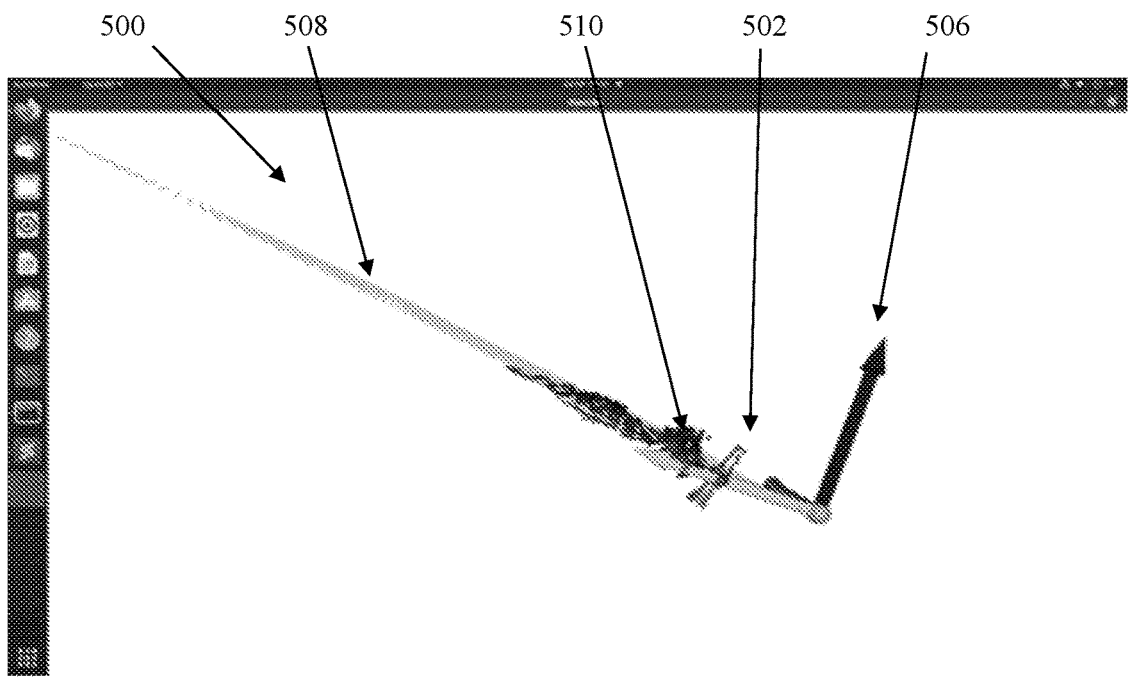
Figure 5C:
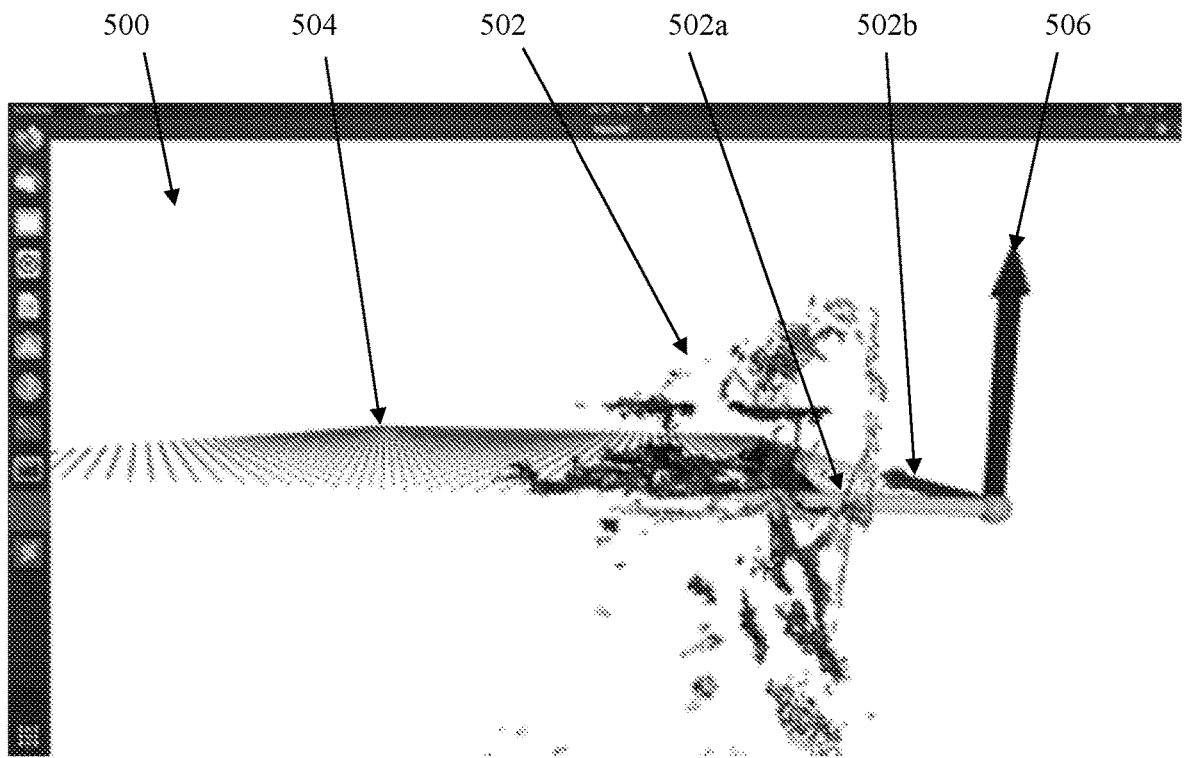

As shown in FIG. 5A, the point cloud is plotted with the table plane mesh 504 (shown in purple). The green arrow 502a (Y axis) is not aligned with the table plane and an offset is illustrated. FIG. 5B depicts an accurate estimation of the table plane despite errors in global alignment, with the thresholded point clouds 510 in brown and the table plane mesh 508 in yellow. After the local alignment step, the misalignment between the coordinate system and the table plane mesh 508 is removed after local alignment. The green arrow should be aligned with the purple mesh 504 and the table in the 3D point cloud as shown in FIG. 5C.

Figure 6A:
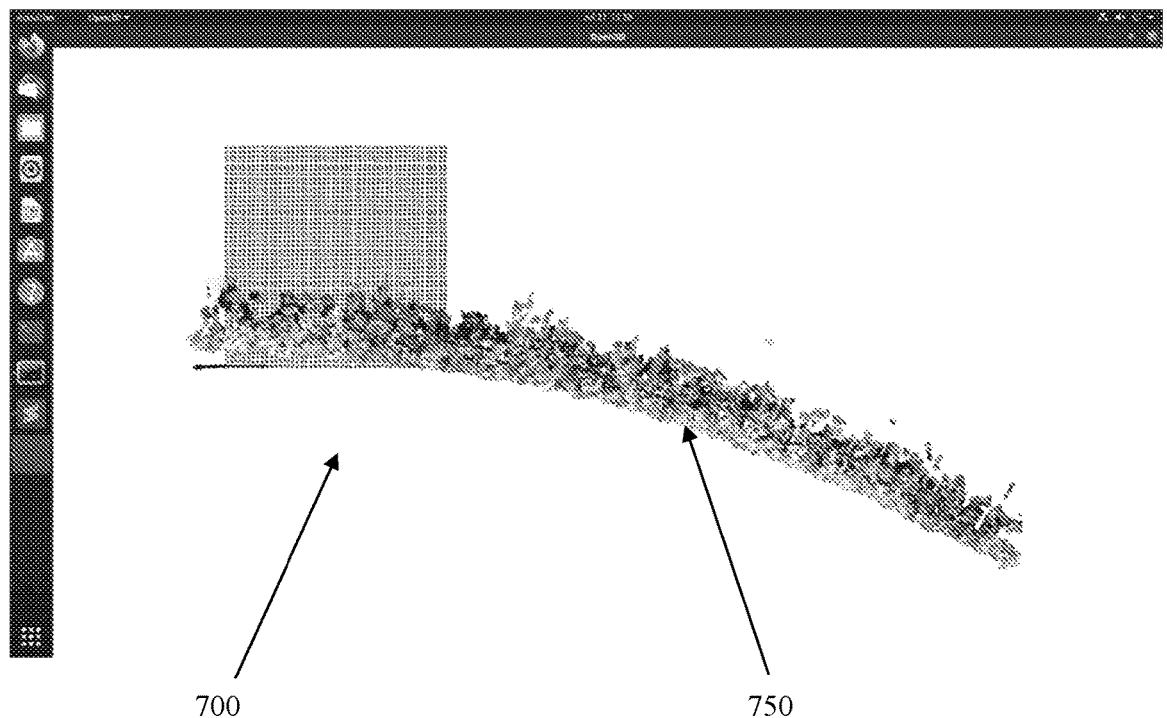
FIGS. 6A and 6B are pictorial representations of a 3D point cloud reconstruction of one plant bench in accordance with one or more embodiments of the disclosure.

The 3D reconstructed scene 700 is generated using a SLAM algorithm that combines the camera IMU and visual odometry. However, errors in pose estimation can build up over time to cause estimated pose to drift from the true pose. This drift 750 is shown in FIG. 6A, which depicts the 3D reconstruction of one plant bench, which is a straight line in real life, but curves across the X-axis. The system is configured to remove the distortions introduced by the SLAM algorithm. The method includes modeling the curved profile of the point clouds as a polynomial curve that is a function of x and finding the transformation that will map these points to a line.

Figure 7:
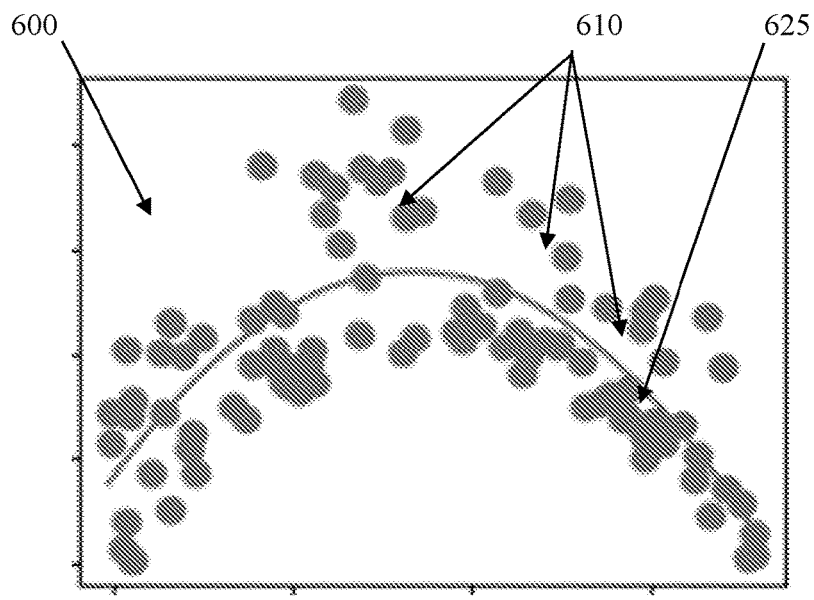
FIG. 7 is a graphical representation of the 3D points mapped into the 2D plane after application of a polynomial degree in accordance with one or more embodiments of the disclosure.

The method includes mapping 3D points to the 2D so that they now sit on the XY plane 600. The Z coordinates of the data are considered to be accurate and can be ignored because of the local alignment step utilized in mapping the point cloud to the world frame. After finding the best fit line for the data, the data is transformed. Obtain the parameters m and b from y=mx+b. Then translate the point cloud so that the best fit line aligns with the x axis. Use a least squares method to find the best fit polynomial to the data. In the example illustrated in FIG. 7, a polynomial degree of 3 was used and shows the sampled 2D points 610 and the fitted polynomial to the curve 625. The points considered for polynomial fitting were randomly sampled with a sample size of 100. The polynomial found p(x) returns y for a value of x.

Figure 6B:
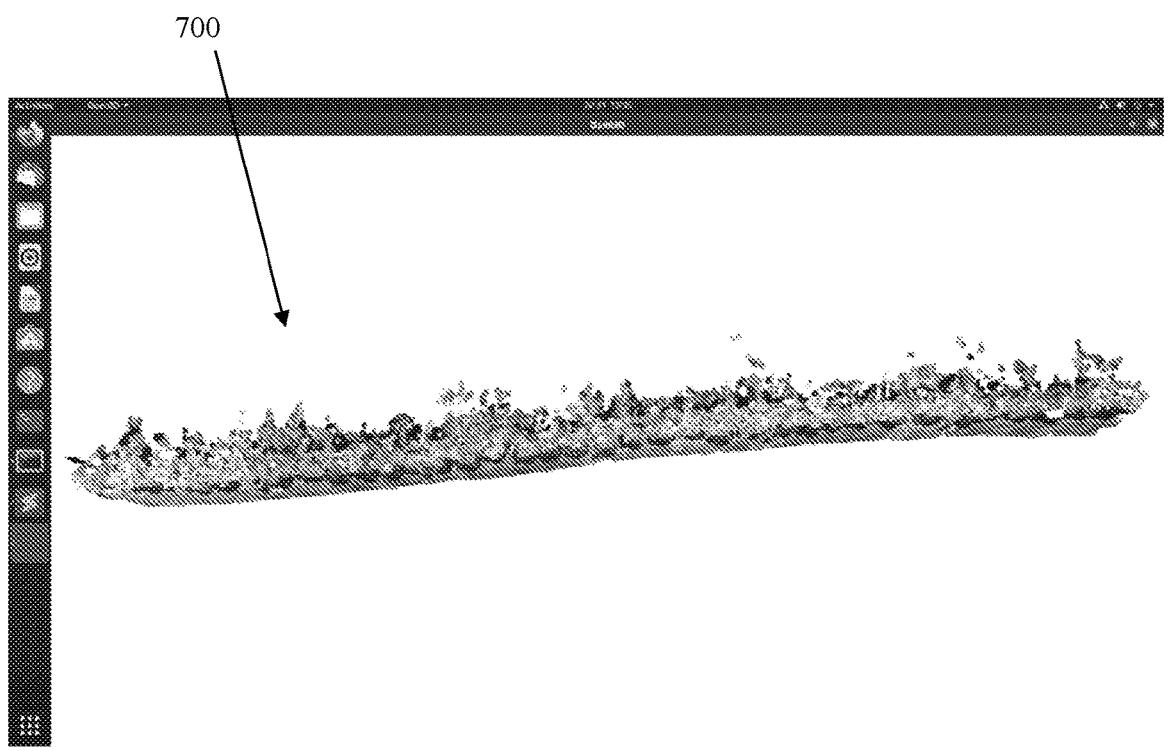

Next, the points are translated according to the polynomial function. Equation: Y_f=Y_0+f (X_0), where the final point cloud coordinates are [X_f, Y_f, Z_f] and the initial coordinates are [X_0, Y_0, Z_0] and Z_f=Z_0 and X_f=X_0. FIG. 6B depicts the 3D transformed point cloud. After the correction, the points clouds are moved so that they are centered along the x axis, which mostly removes the curved distortions. While the larger distortion is removed, there is still an artifact present and the bench is not completely straight. Changing the sampling method/number of samples and/or the polynomial degree that are considered in the fitting of the dataset to a polynomial should improve the result. After this process is carried out, the Z coordinate of each point is preserved. As such, projecting to 3D can be done simply by adding the original Z coordinate to each associated 2D point.

After carrying out the steps described above, the pot positions are relatively easy to extract. To extract the pot positions, the system filters the points so that only the points that are within a certain threshold of the pot rim height are kept. These points can be projected onto the 2D, and then further clustering and filtering is done to extract the pot positions. Specifically, the pot heights can be used as filter points, because the system knows the exact height of the pots it filters points by their z axis values, only keeping points that are within a certain threshold of the pot rim height. The filtered points are projected onto an occupancy grid. For example, the 3D points are mapped to 2D and the system creates a 2D occupancy grid, scaled by the voxel size used to down-sample the 3D points. The 2D points are mapped to a cell in the occupancy grid, where each item in the occupancy grid is either set to 1 or 0 depending on if a 2D point is mapped to it or not.

Next, a clustering algorithm (e.g., the Hoperoft-Karp Clustering Algorithm) is used to generate a list of clusters where cells in the occupancy grid that share an edge are assigned to the same cluster. A typical pot has a certain dimension and when mapped to the occupancy grid, that dimension should correspond to some area value (e.g., right sizes). If it is within some minimum and maximum threshold, it is accepted as a pot. The coordinates of the centroid are chosen as the pot positions. However, if the cluster area is too small compared to a typical pot area, it is rejected. If it is too large, then it is passed for further processing.

In some cases, large clusters could actually be multiple set of pots that just happen to belong to the same cluster when it was projected into 2D. This is likely because the pots were too close to begin with. In order to separate these pots, the system estimates the number of plants using the ratio K, where K is equal to (total_cluster_area)/(typical_pot_area). This is the value of K that is passed into a Kmeans algorithm for segmentation. The Kmeans process should divide up the overlapping clusters into K separate clusters. The centroids of these new clusters are then returned as plant centers. Large cluster processing benefits from tuning of the thresholds from finding the right size clusters and the estimation of the typical pot size.

Figure 8:
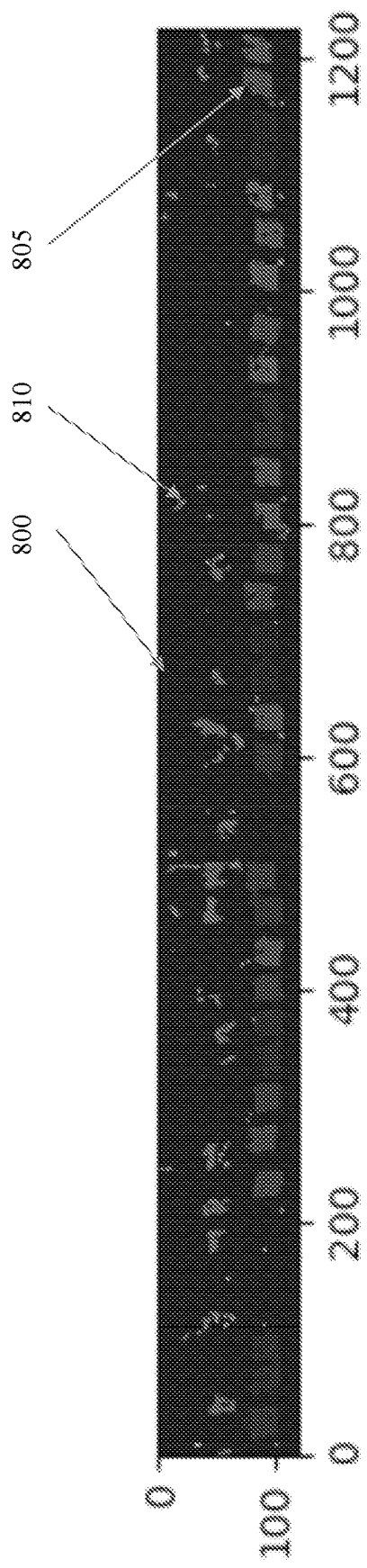
FIG. 8 is a pictorial representation of two plots showing a scanned section of a growing facility before and after filtering and segmentation of the data in accordance with one or more embodiments of the disclosure.
Figure 8:
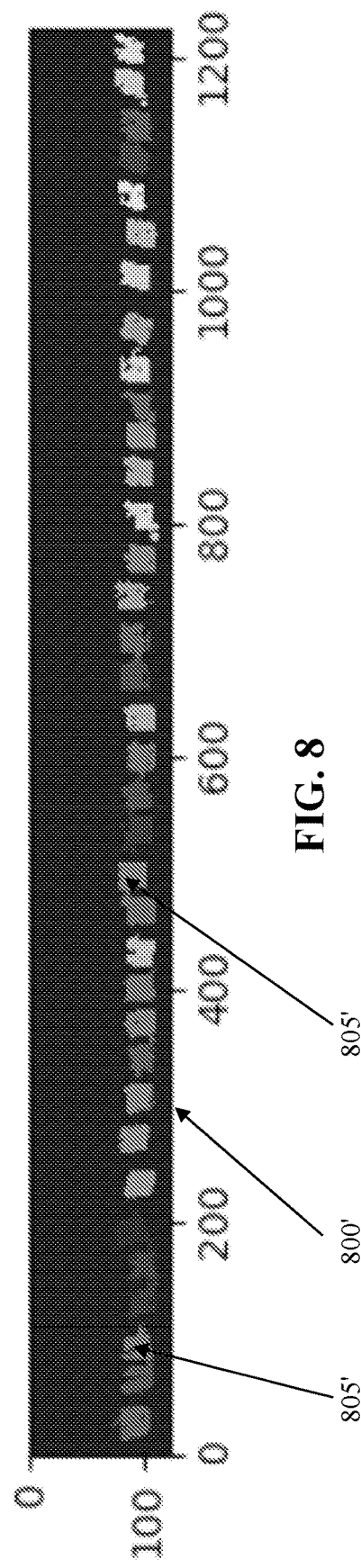
Figure 9:
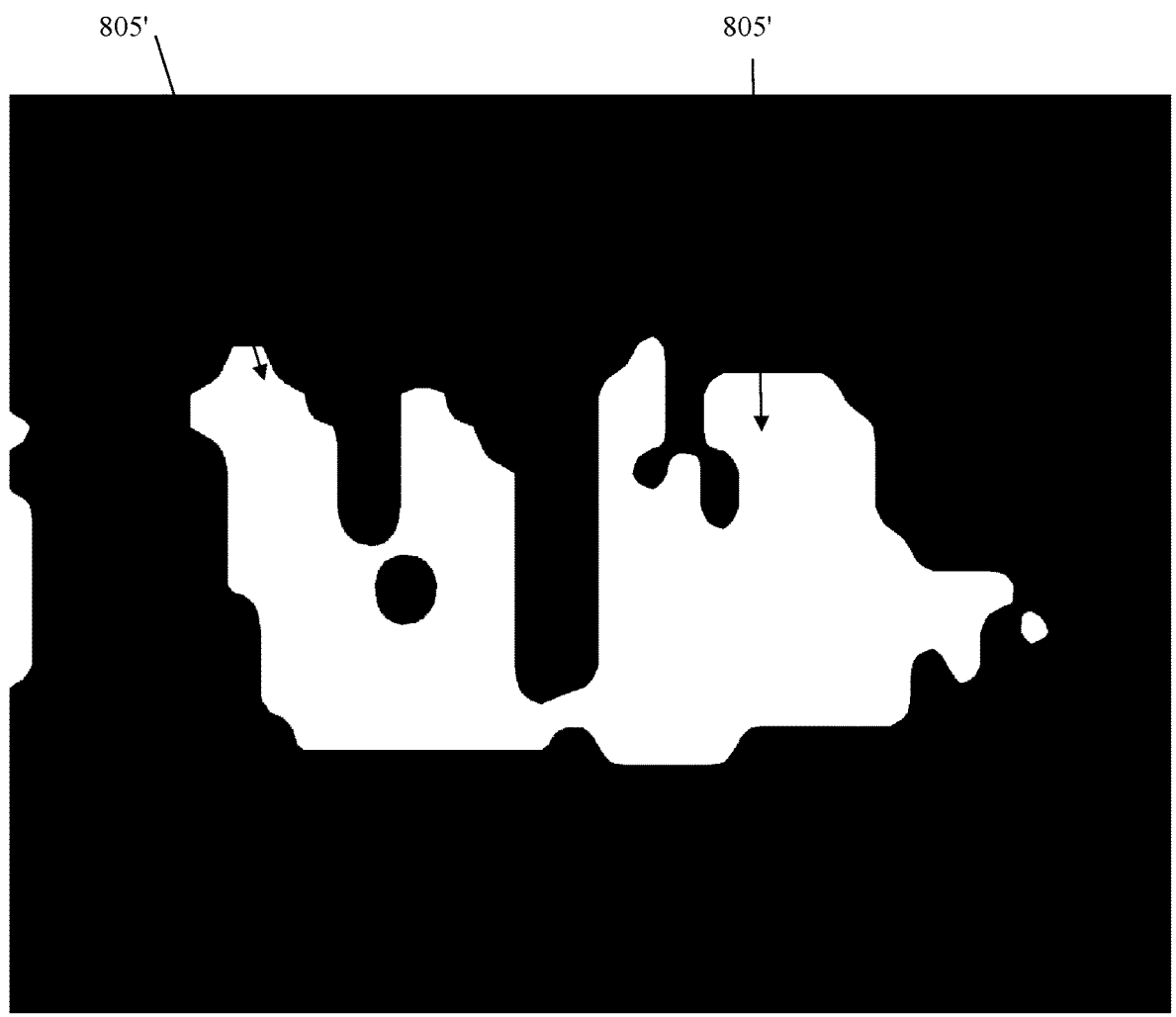
FIG. 9 is an enlarged pictorial representation of abutting clusters generated via a Kmeans algorithm in accordance with one or more embodiments of the disclosure.

The result of this process is shown in FIG. 9, while FIG. 8 depicts the occupancy grid after application of the clustering algorithm (top plot) and the Kmeans algorithm (bottom plot). Specifically, the top plot of FIG. 8 depicts the clustered occupancy grid 800 and includes a lot of small clusters 810 that are not pots. The bottom plot of FIG. 8 depicts the clustered occupancy grid 800' after filtering and segmentation based on area, where only cells 805' that confidently correspond to pots are colored. The different colors are used to distinguish between different pots. FIG. 9 is a close-up of a cluster 805' that is touching (technically two abutting clusters) and was originally recognized as only a single cluster after using the Hoperaft-Karp algorithm. The Kmeans algorithm is able to segment the abutting clusters into two separate clusters.

The images captured, generated or otherwise derived from the captured images may be further enhanced by, for example, using two cameras (e.g., both on a sensing unit, one camera located on the sensing unit and a second camera or cameras located throughout the facility, or any number of cameras on individual drones). In order to infer plant height from the 3D reconstruction, the system can use data from the point cloud of the canopy and integrate these two sets of point clouds. In some cases, this also results in a curved profile that might not necessarily match the profile of the pot scene, making it difficult to directly transform the points into the correct position. In some embodiments, a new point cloud topic is created in ROS that has the integrated point clouds from the pot camera point of view. The SLAM mapper is used to map this point cloud. The method takes segments of the canopy point cloud and uses the iterative closest point (ICP) or random sample consensus (RANSAC) algorithm to match them in the right place; however, incorrect matching may occur. This may be improved by overlap between the two points clouds, with greater overlap resulting in fewer errors. In this method, the ROS code uses the rtab_map library and the launch file is based off the demo_two_kinect.launch: link.

Figure 10:
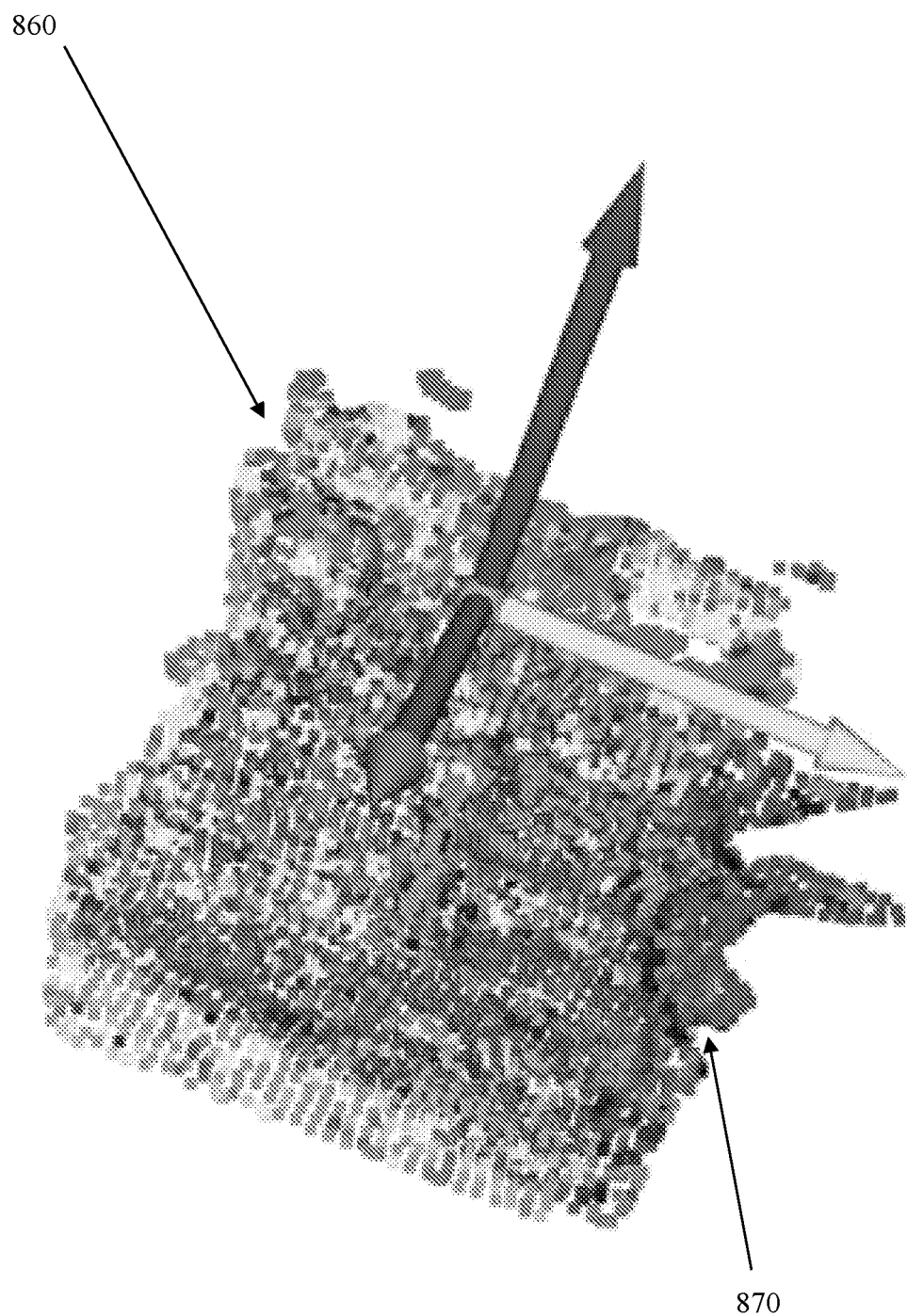
FIG. 10 is a pictorial representation of aligned point clouds in accordance with one or more embodiments of the disclosure.

The transformation between the two cameras must be accurate in order to combine the two sets of point clouds. Manually measuring the transform between the two cameras is both cumbersome and prone to errors, because the positions of the cameras have to be adjusted often to accommodate different data capturing scenarios. Accordingly, measuring the transform every time is very labor intensive and undesirable and, therefore, a computational approach is used. The computational approach uses the open3D registration library for RANSAC and ICP to find the transformation between two sets of point clouds. The result of running this algorithm is shown in FIG. 10. As shown, the two previously unaligned point clouds 870, 860 (shown in red and teal) are aligned. This computed transform needs to be converted into the ROS coordinate system. A library called pyrealsense, which was used to save the point clouds for calibration, saves the point clouds using a different coordinate system than the one dual camera ROS program uses for the 3D Reconstruction. In FIG. 10, the red, green, and blue arrows correspond to the x- y- and z-axes.

The data captured (and processed) by the sensing unit can be associated with the post-harvest data collected at various stages of material processing. This data can then be used for supervised or unsupervised training of statistical/machine learning models for quality grading/scoring. Additionally, the data collected by the sensing unit from all the post-harvest plant material, which will be processed for extraction together at a later time, can be used for inference and prediction of yield quality and volume, can be used to modify the recipe of how the material will be processed in the following steps in the entire process of delivering it to an end-user or a customer, or inform any decisions made throughout that process such as pricing, etc.

Having now described some illustrative embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives.

Furthermore, those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is, therefore, to be understood that the embodiments described herein are presented by way of example only and that, within the scope of any appended claims and equivalents thereto; the invention may be practiced other than as specifically described.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to any claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish claim elements.

What is claimed is:

1. A method of generating contextually rich plant images comprising:
   generating a plurality of data captures of raw plant data via a sensing unit configured to navigate rows of plants within a growing facility;
   generating and assigning metadata to the raw plant data including at least one of: plant location, timestamp, plant identification, plant strain, facility identification, facility location, facility type, health risk factors, plant conditions, and human observations;
   analyzing images generated by the sensing unit and generating pixel annotations in the images based on their relation to one or more plant well-being features;
   assigning data tags to one or more of the plurality of data captures based on an analysis of the plurality of data captures, wherein the data tags are text phrases linking a particular data capture to a specific threat to plant well-being;
   performing image processing on the images generated by the sensing unit, the image processing including at least one of:
      transforming an image by cropping the image into a smaller image, reducing noise, modifying sharpness or brightness, or performing color balancing;
      stitching two or more images together to generate a panorama image to minimize double counting plant regions;
      overlaying different images of a single scene collected with different cameras; or
      cropping a panorama image to fit a particular aspect ratio;
   generating a database query based on user input received from a user interface;
   comparing user input received from the user interface against the data tags assigned to one or more of the plurality of data captures; and
   generating a curated data set including a subset of the plurality of data captures corresponding to a combination of the tags, based on the comparison with the user input.

2. The method of claim 1, wherein the plurality of data captures includes a collection of images across visible and non-visible light spectra.

3. The method of claim 1, wherein the plurality of data captures includes a collection of thermal images.

4. The method of claim 1, wherein the plurality of data captures includes a collection of environmental readings comprising at least one of: temperature, humidity, luminosity, radiation, magnetic field, particulate matter, and chemical compounds.

5. The method of claim 1, wherein the plurality of data captures includes a collection of contextual readings comprising at least one of: acceleration, gyroscope position, orientation, previous system state, next planned system state, power level, CPU usage, CPU memory, and communication signal.

6. The method of claim 4, further comprising:
   generating a database containing:
      the raw plant data from the plurality of data captures;
      the metadata assigned to the raw plant data;
      the pixel annotations in the images; and
      the data tags assigned to one or more of the plurality of data captures.

7. The method of claim 1, further comprising:
   generating a plant profile for one or more plants within the growing facility, wherein each plant profile includes:
      a plant identifier identifying a particular plant;
      sensor information generated by the sensing unit related to the particular plant;
      metadata related to raw plant data of the particular plant; and
      data tags related to raw plant data of the particular plant.

8. A method of training a machine learning model comprising:

querying a database containing raw plant data from a plurality of data captures, metadata assigned to the raw plant data, pixel annotations in images analyzed from the plurality of data captures, and data tags assigned to one or more of the plurality of data captures wherein the data tags are text phrases linking a particular data capture to a specific threat to plant well-being, wherein the database query includes at least one tag or data parameter;

generating a curated training data set including a subset of the plurality of data captures corresponding to the at least one tag or data parameter;

selecting one or more features from the pixel annotations in images analyzed from the plurality of data captures;

building a trained machine learning model based on an analysis of the curated training data set and the one or more features, wherein the trained machine learning model is configured to:
 receive raw plant data from the plurality of data captures;
 associate a subset of the raw plant data with the one or more features; and
 identify an existence of one or more plant abnormalities within the subset of the raw plant data based on the association of the subset with the one or more features;

analyzing raw plant data from previous data captures associated with a particular plant to associate earlier data features with the one or more plant abnormalities when the trained machine learning model identifies the existence of the one or more plant abnormalities within the particular plant, wherein analyzing raw plant data from previous data captures comprises overlaying images of the particular plant from different time intervals to detect a pattern in raw plant data prior to detecting a visible plant abnormality.

9. The method of claim 8, wherein the at least one tag or data parameter includes a text phrase related to a specific threat to plant well-being, such as disease, insects, pest activity, dehydration, nutrient deficiencies, future diseases, harvest yield, or harvest time.

10. The method of claim 8, wherein the images analyzed from the plurality of data captures include thermal images depicting temperature variations within one or more plants, and the trained machine learning model is configured to identify the existence of one or more plant abnormalities within the subset of the raw plant data based on the temperature variations.

11. The method of claim 8, wherein the trained machine learning model is an artificial neural network comprising a plurality of input nodes, one or more hidden layers, and a plurality of output nodes, wherein each input node includes a memory location for storing input values including the raw plant data from the plurality of data captures.

12. The method of claim 8, further comprising generating a plurality of risk scores corresponding to the one or more plant abnormalities.

* * * * *